(12) United States Patent
Surma et al.

(10) Patent No.: US 7,300,432 B2
(45) Date of Patent: Nov. 27, 2007

(54) APPARATUS FOR SECURING A SENSOR TO A SURGICAL INSTRUMENT FOR USE IN COMPUTER GUIDED ORTHOPAEDIC SURGERY

(75) Inventors: Gabriel Surma, Winona Lake, IN (US); Troy David Martin, Pierceton, IN (US); James Edward Clark, Warsaw, IN (US); Jack Theodore Bryant, Warsaw, IN (US)

(73) Assignee: DePuy Products, Inc., Warsaw, IN (US)

(*) Notice: Subject to any disclaimer, the term of this patent is extended or adjusted under 35 U.S.C. 154(b) by 628 days.

(21) Appl. No.: 10/828,778

(22) Filed: Apr. 21, 2004

(65) Prior Publication Data

US 2005/0238418 A1    Oct. 27, 2005

(51) Int. Cl.
*A61B 17/00* (2006.01)
(52) U.S. Cl. ........................................... 606/1
(58) Field of Classification Search ............ 606/1; 248/127, 239, 635
See application file for complete search history.

(56) References Cited

U.S. PATENT DOCUMENTS 3,713,611 A * 1/1973 Voigt .................... 248/539
5,520,694 A    5/1996 Dance et al.
5,603,318 A    2/1997 Heilbrun et al.
6,223,067 B1   4/2001 Vilsmeier et al.
2002/0107518 A1  8/2002 Neubauer et al.
2003/0153829 A1  8/2003 Sarin et al.
2003/0153978 A1  8/2003 Whiteside

OTHER PUBLICATIONS

European Search Report for European Patent Application No. 05252253.9-2318, Aug. 4, 2005, 3 pgs.
Smith & Nephew, Inc. AchieveCAS Computer Assisted Surgery brochure, entitled Innovations In Minimally Invasive Joint Surgery, dated Feb. 2004, 8 pages.

* cited by examiner

*Primary Examiner*—Michael Peffley
*Assistant Examiner*—Pete Vrettakos
(74) *Attorney, Agent, or Firm*—Barnes & Thornburg LLP

(57) ABSTRACT

A self-centering coupling device is provided for coupling a sensor array to a surgical instrument for use in computer guided surgery. The self-centering coupling device includes a sensor support having a stem and sensor support arms coupled to the stem to support the sensors of the sensor array. The self-centering coupling device is received within a recess formed in the surgical instrument.

24 Claims, 8 Drawing Sheets

APPARATUS FOR SECURING A SENSOR TO A SURGICAL INSTRUMENT FOR USE IN COMPUTER GUIDED ORTHOPAEDIC SURGERY

FIELD OF THE DISCLOSURE

The present disclosure relates generally to a sensor used in computer guided orthopaedic surgery, and more specifically to coupling devices use in computer guided orthopaedic surgery.

BACKGROUND

Many computer guided orthopaedic surgical procedures are based on determining the position of bones, and relating this position into the computer via some type of ultrasonic, magnetic resonance, or optical sensor. A similar sensor is attached or contained within the surgical instrument and subsequently guided via a computer into the desired position within the patient. U.S. Patents and patent Publications relating to computer guided surgery include U.S. Pat. No. 5,520,694 and U.S. Patent Application Publication Nos. 2003/0153978 A1 and 2003/01538829 A1, each of which is hereby incorporated by reference. Similar computer guided navigation systems are disclosed in U.S. Pat. Nos. 6,514,259; 6,434,507; 6,428,547; 6,424,856; 6,351,659; 6,223,067; 6,187,018; 6,178,345; 5,889,834; 5,769,861; 5,702,406; 5,643,268; and 5,628,315, along with U.S. Patent Application Publication No. 2002/0038118 A1, each of which is hereby incorporated by reference. The accuracy of this guidance is dependent on various factors including, for example, computer hardware and software resolution, the location of the sensor on the surgical instrument, and manufacturing tolerances of the sensor and its attachment mechanism to the surgical instrument.

Tight manufacturing tolerances often result with increased cost of the attachment mechanism and require precise alignment of the components before assembly. This may decrease the user-friendliness of the operation of the attachment mechanism. In an operating room environment, for example, and particularly with the advent of minimally invasive surgery, the maneuvering space available to the surgeon becomes increasingly smaller. Precise alignment of tightly machined components having small tolerances may be difficult.

SUMMARY

The present disclosure comprises one or more of the features recited in the appended claims or one or more of the following features or combinations thereof.

According to one aspect of the present disclosure, a self-centering coupling device is used for securing a sensor to a surgical instrument for use in computer guided orthopaedic surgery. The device includes a sensor support having a support arm to support the sensor and a stem having a first end secured to the support arm. A second end of the stem is expandable between a first position in which the second end of the stem has a first width and a second position in which the second end of the stem has a second, larger width.

The device may further include a pin or fastener to secure the sensor support to the surgical instrument. The pin moves the second end of the stem from the first position to the second position. According to one illustrative embodiment, the stem includes a passageway defined by an inner sidewall. The inner sidewall is tapered at the second end of the stem. Insertion of the pin into the passageway causes the second end of the stem to be moved from the first position to the second position.

According to another aspect of the present disclosure, the sensor support is constructed with a polymeric material. In one illustrative embodiment, the sensor support is constructed with a polycarbonate plastic.

According to yet another aspect of the present disclosure, a surgical instrument used in computer guided orthopaedic surgery includes a body having a recess configured to receive a sensor support. The recess is defined by a first side wall, a second side wall, and a bottom wall. The first side wall and the second side wall are inclined relative to one another. The recess is further defined by a third side wall and a fourth side wall such that the third and fourth side walls are inclined also relative to one another. The first side wall and the second side wall are arranged in a substantially V-shaped configuration and the third side wall and the fourth side wall are arranged in a substantially V-shaped configuration.

According to still another aspect of the present disclosure, a method of attaching a sensor support carrying a sensor array to a surgical instrument for use in computer guided orthopaedic surgery includes positioning an end of the sensor support into a recess formed in the surgical instrument and inserting a pin into a passageway of the sensor support to urge outer walls of the sensor support to contact with a number of side walls of the recess.

According to yet another aspect of the present disclosure, a method of using a computer guided orthopaedic surgical instrument includes removing a first sensor support from a first sterile package, securing the first sensor support to the surgical instrument with a sterile fastener, performing a first computer guided orthopaedic surgical procedure, removing the fastener and the first sensor support from the surgical instrument, disposing of the first sensor support, sterilizing the fastener for use in a second computer guided surgical procedure, removing a second sensor support from a second sterile package, securing the second sensor support to the surgical instrument with the fastener, and performing a second computer guided orthopaedic surgical procedure.

The above and other features of the present disclosure will become apparent from the following description and the attached drawings.

DETAILED DESCRIPTION OF THE DRAWINGS

Figure 1:
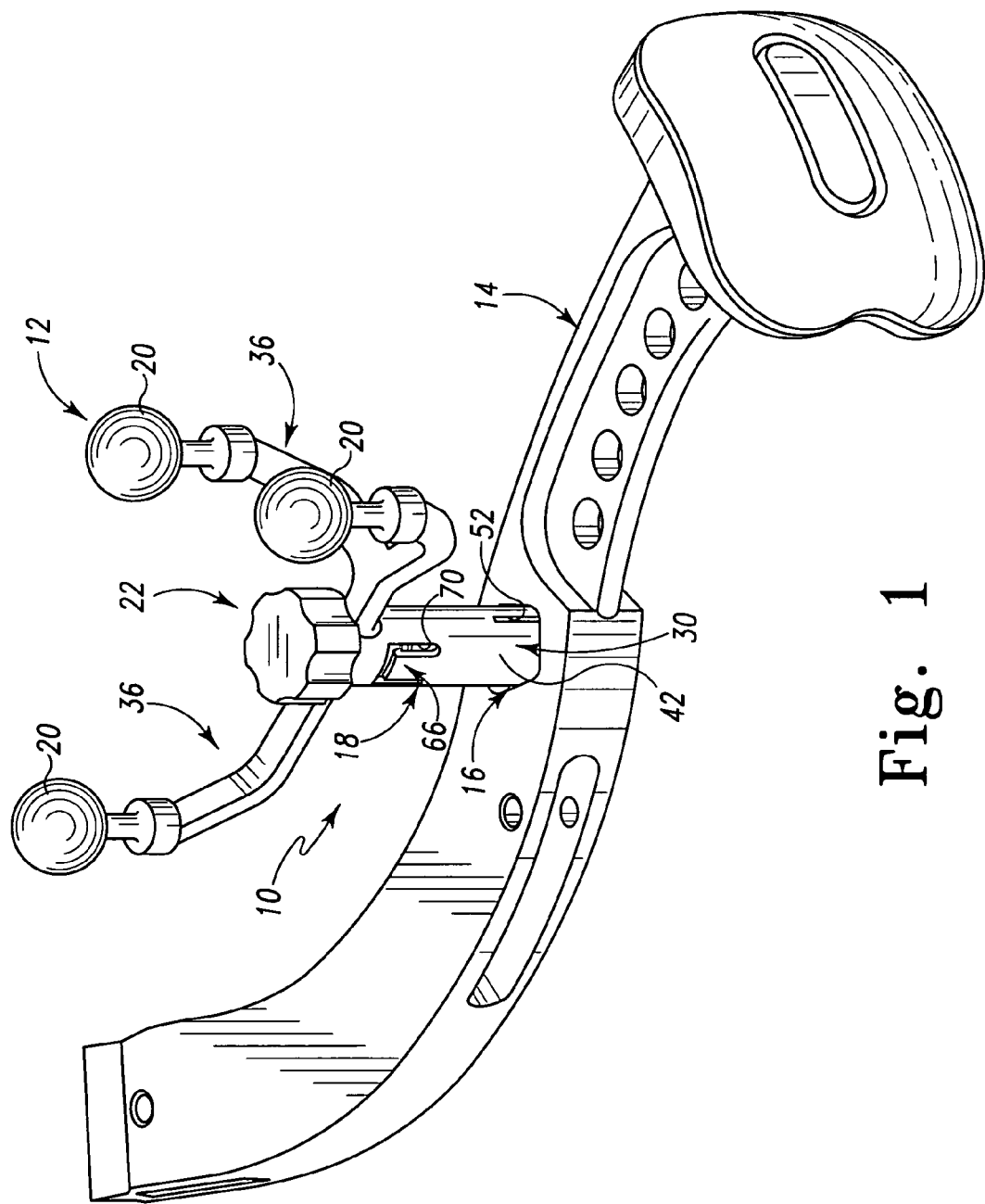
FIG. 1 is a perspective view of a portion of an orthopaedic broach having a sensor array coupled to the broach by a self-centering coupling device.
Figure 2:
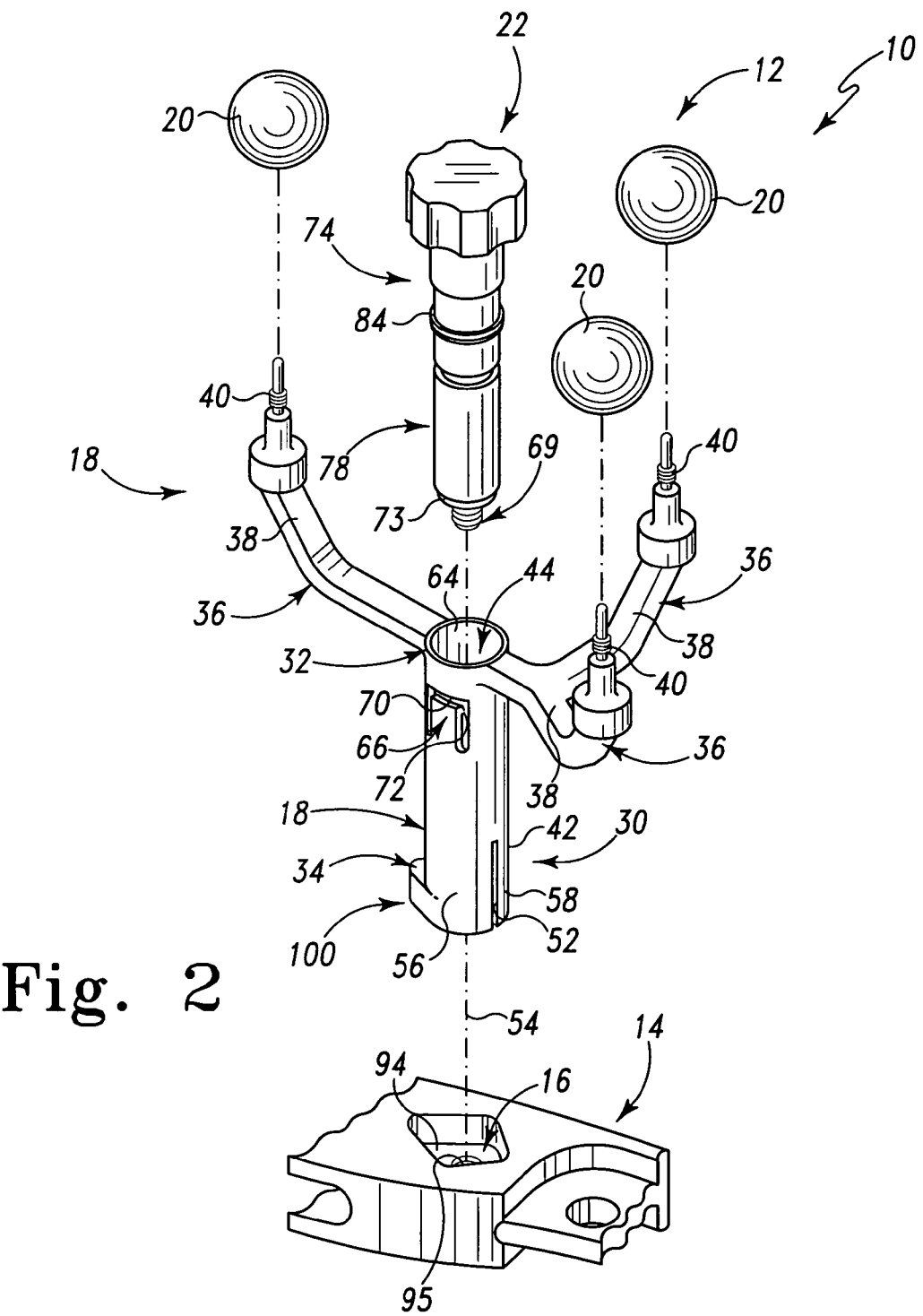
FIG. 2 is an exploded, perspective view of the self-centering coupling device of FIG. 1.

A self-centering coupling device 10 is used to attach a computer-guided sensor array 12 onto a surgical instrument such as a broach handle 14, shown in FIG. 1, for example. The self-centering coupling device 10 is received into a generally diamond-shaped recess 16 formed in the broach handle 14 (as shown in FIG. 2). The device 10 includes a sensor support 18 that supports spherical sensors 20 of sensor array 12 and a fastener or pin 22 that couples the sensor support 18 to the surgical broach handle 14. In general, the sensor array 12 and the coupling device 10 are used during computer guided orthopaedic surgical procedures. The sensor array 12, when coupled to the broach handle 14 shown in FIG. 2, is used by a navigation system to track the position of the broach handle 14 during surgery. Although herein described in regard to a broach handle, the self-centering coupling device 10 may be used to support the sensor array 12 on or any other type of surgical instrument used during computer guided orthopaedic surgery or other surgical procedures as well.

Looking now to FIG. 2, the sensor support 18 includes a stem 30 having a first or distal end 32 and a second or proximal end 34. First, second, and third sensor support arms 36 are each coupled to the distal end 32 of stem 30. Each sensor support arm 36 includes an arm portion 38 and a threaded shaft 40 coupled to an outer end of the arm portion 38. Illustratively, each spherical sensor 20 includes a threaded bore 41 formed to receive the threaded shaft 40 of one of the sensor support arms 36 in order to couple each sensor 20 to the sensor support 18. The sensors 20 may be ultrasonic, magnetic resonance, or optical sensors, for example. Sensors 20 are commercially available from Brain-LAB AG of Heimstetten, Germany.

Figure 4:
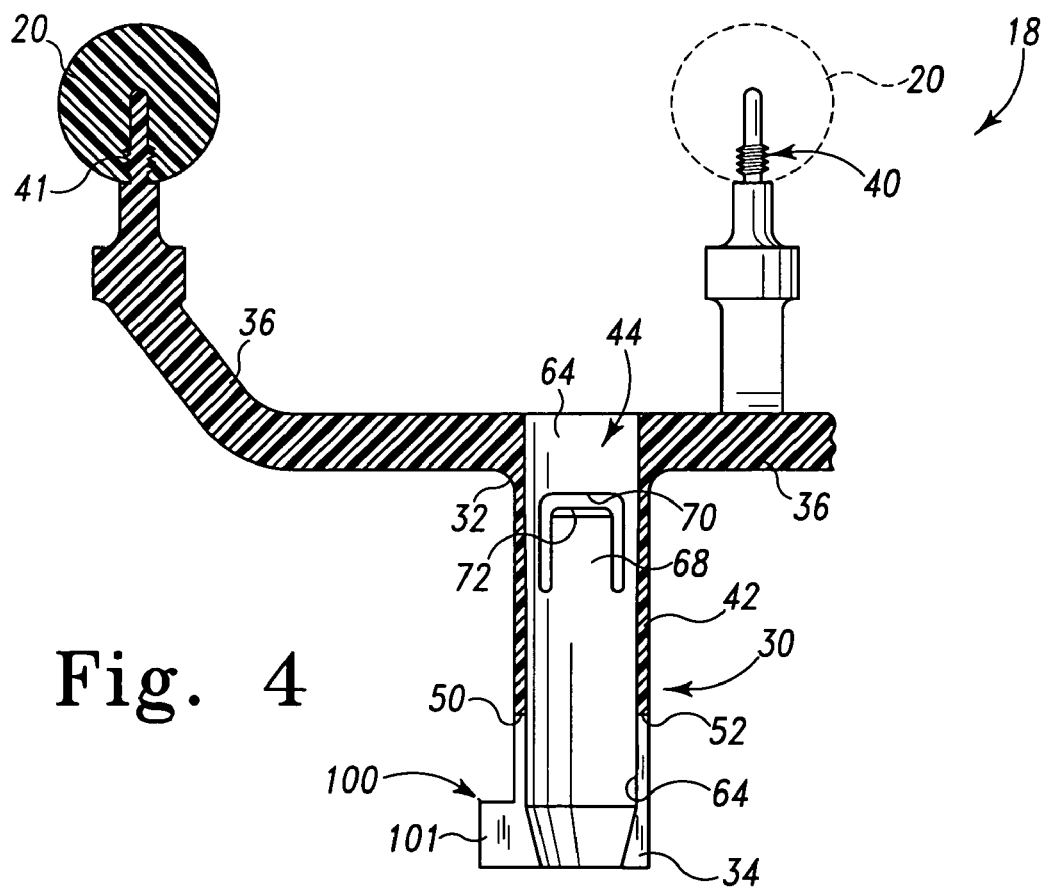
FIG. 4 is a sectional view of the sensor support taken along line 4-4 of FIG. 3.

The stem 30 of the sensor support 18 includes a generally cylindrical outer wall 42 defining a passageway 44 between distal end 32 and proximal end 34. As shown in FIG. 4, a proximal end portion of passageway 44 is tapered and is shown to narrow at the proximal end 34 of the stem 30. As is discussed in greater detail below, the walls of passageway 44 are engaged by pin 22 to expand the proximal end 34 of the stem 30 outwardly when the pin 22 is inserted through the passageway 44 and engages the narrowed, proximal end portion of passageway 44.

Figure 3:
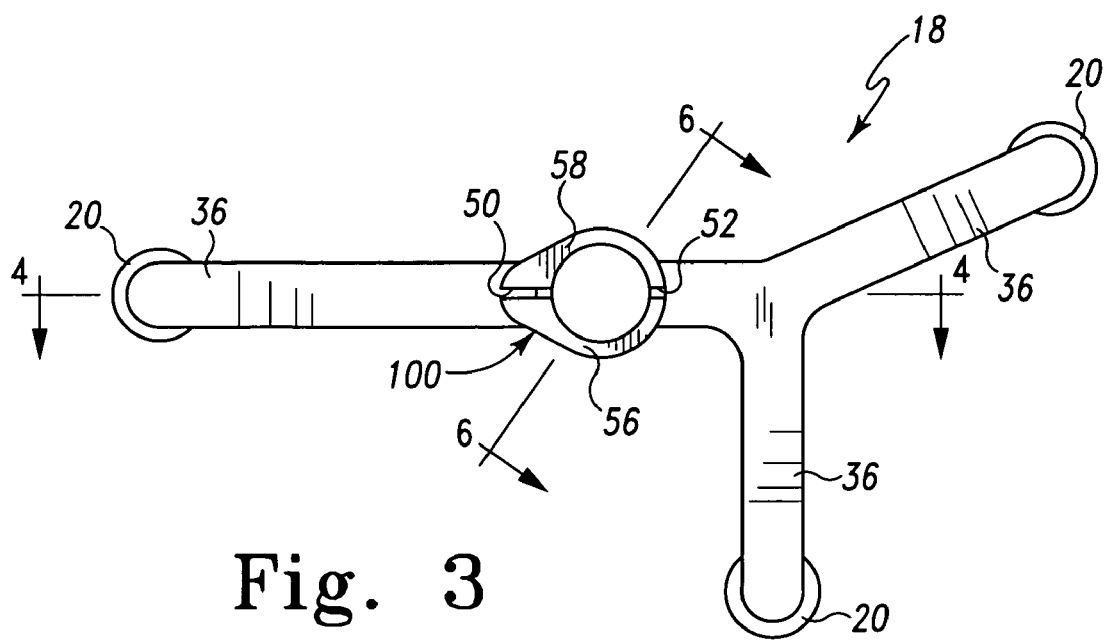
FIG. 3 is a bottom view of the sensor support of the self-centering coupling device of FIG. 1.

The stem 30 of the sensor support 18 further includes first and second longitudinal slots 50, 52 formed in outer wall 42, as shown in FIGS. 2 and 4. Illustratively, slots 50, 52 extend from the proximal end 34 of the stem 30 toward the distal end 32 and are parallel to a vertical axis 54 defined along a length of the stem 30. Slots 50, 52 are positioned approximately 180° apart from each other about vertical axis 54 as viewed in FIG. 3, for example, and extend from the proximal end 34 of stem 30 toward the distal end 32 of stem 30 approximately a distance less than half a length of stem 30.

Slots 50, 52 cooperate to define first and second outer wall portions 56, 58 of outer wall 42. As is discussed in greater detail below, outer wall portions 56, 58 are movable between a first position shown in FIGS. 3 and 9 where the slots 50, 52 have a first width 60 at the proximal end 34 of stem 30, and a second position shown in FIG. 10 where the slots 50, 52 have a second width 62 at the proximal end 34 of stem 30. The second width 62 is greater than the first width 60 such that the ends of the outer wall portions 56, 58 are positioned a greater distance away from each other (as viewed from the bottom of sensor support 18) thereby engaging the side walls of recess 16. Note that the opening defined by passageway 44 at the proximal end 34 of stem 30 increases in size in a similar manner as slots 50, 52 when the pin 22 is inserted within passageway 44.

Figure 9:
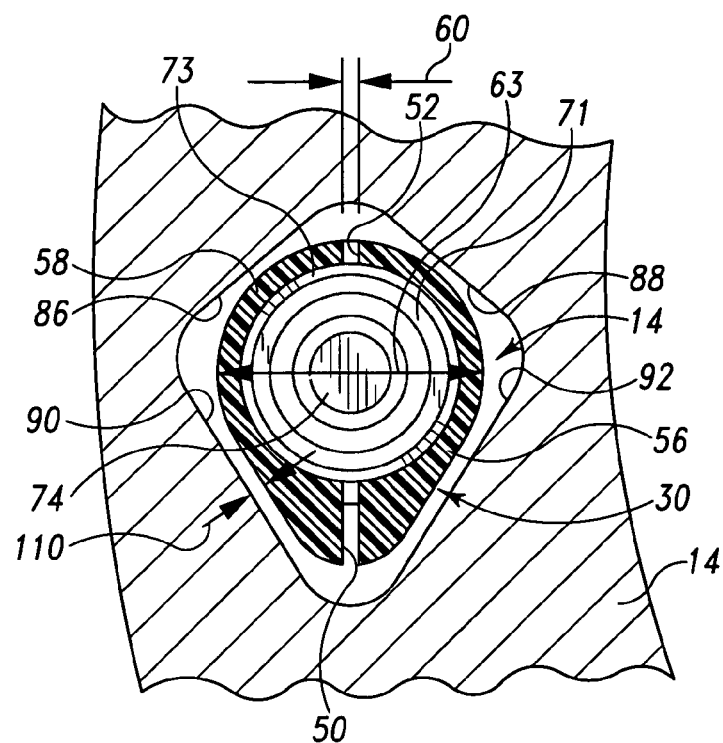
FIG. 9 is a sectional view taken along line 9-9 of FIG. 6.
Figure 10:
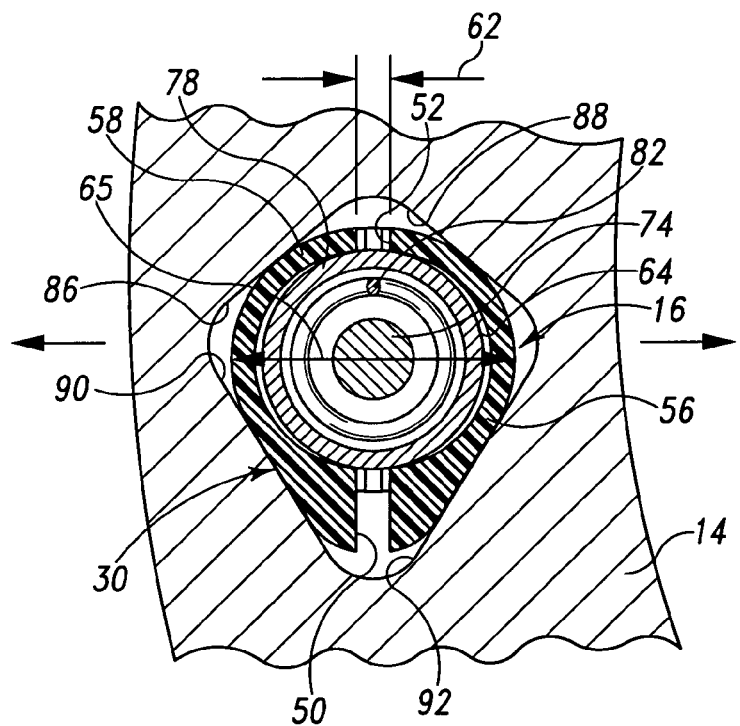
FIG. 10 is a sectional view similar to FIG. 9 that is taken along line 10-10 of FIG. 8.

Further, proximal end 34 of stem 30 has a first width, 63, when stem 30 is in the first position, as shown in FIG. 9, and a second width, 65, when stem 30 is in the second position, as shown in FIG. 10. Second width, 65, is greater than first width, 63. As shown in FIGS. 9 and 10, first and second widths, 63 and 65, are illustratively taken through a center of stem 30. However, a width taken between any two opposite points of the proximal end 34 of the stem 30 increases as proximal end 34 of stem 30 is moved from the first position to the second position.

As is discussed in greater detail below, insertion of the pin 22 into the passageway 44 of the stem 30 expands the proximal end 34 of the stem 30 of the sensor support 18 by urging outer wall portions 56, 58 outwardly away from one another. The diameter of the tapered portion of passageway 44 is smaller than the diameter of the pin 22 inserted in passageway 44 such that the pin 22 acts against an inner surface or side wall 64 of the tapered portion of passageway 44 (defined by outer wall portions 56, 58) to move outer wall portions 56, 58 to their expanded positions.

Looking now to FIGS. 2 and 6-8, stem 30 of sensor support 18 further includes anti-backout catches or tabs 66, 68. Each tab 66, 68 is formed by a generally "U-shaped" slot 70 formed in outer wall 42 of stem 30 such that each tab 66, 68 is anchored to outer wall 42 at one end and movable relative to the outer wall 42 at the other end. Each tab 66, 68 further includes a lip 72 extending inwardly into the passageway 44 of stem 30. As is discussed below, the lip 72 of each tab 66, 68 engages a portion of the pin 22 as the pin 22 is inserted into the passageway 44. The tabs 66, 68 operate as anti-backout catches or tabs to maintain the pin 22 within the passageway 44 and to prevent the pin 22 from unintentionally being removed from within the passageway 44 once inserted.

Sensor support 18 further includes a generally teardrop-shaped foot 100 formed by a lobe 101 at the proximal end 34 of stem 30. Foot 100 includes a portion of each outer wall portion 56, 58, as shown in FIGS. 2, 9, and 10. As is discussed below, foot 100 allows a user to key or otherwise properly orient the sensor support 18 in a certain position with respect to the broach handle 14 when coupling the sensor support 18 to the broach handle 14. Each sensor 20 of the sensor array 12 is to be oriented or positioned in a particular manner in order to relay the proper position of the broach 14, to which the sensors 20 are attached, back to the main computer, for example. The foot 100 of the sensor support 18, therefore, allows the user to quickly and easily orient the sensor support 18 (and sensor array 12 thereon) in the proper position.

Illustratively, sensor support 18 is made by injection molding a polymeric material into a mold. The disclosure herein, however, is not limited by the injection molding process. In a specific exemplary embodiment, sensor support 18 is made from polycarbonate plastic. Other suitable plastics, such as polyethylene or high density polyethylene, for example may be used as well. For example, the sensor support 18 may comprise a plastic selected from the group consisting of acrylic, epoxy, polyester, polypropylene, polyurethane, polyethylene, polycarbonate, polystyrene, polysulfone, polyetherimide, polyethersulfone, polyphenylsulfone, polyphenylsulfide, acrylonitrile-butadiene-styrene polymer, polyetheretherketone, and combinations thereof. It should be appreciated that other types of thermosetting or thermoplastic resins may be used to fit the needs of a given design. Because sensor support 18 is made of a plastics material and is able to be mass produced by injection molding, for example, a generally low cost and disposable device is able to be produced. Further, the disposability of the sensor support 18 provides that the sensor support 18 does not need to be recalibrated after every use.

Figure 5:
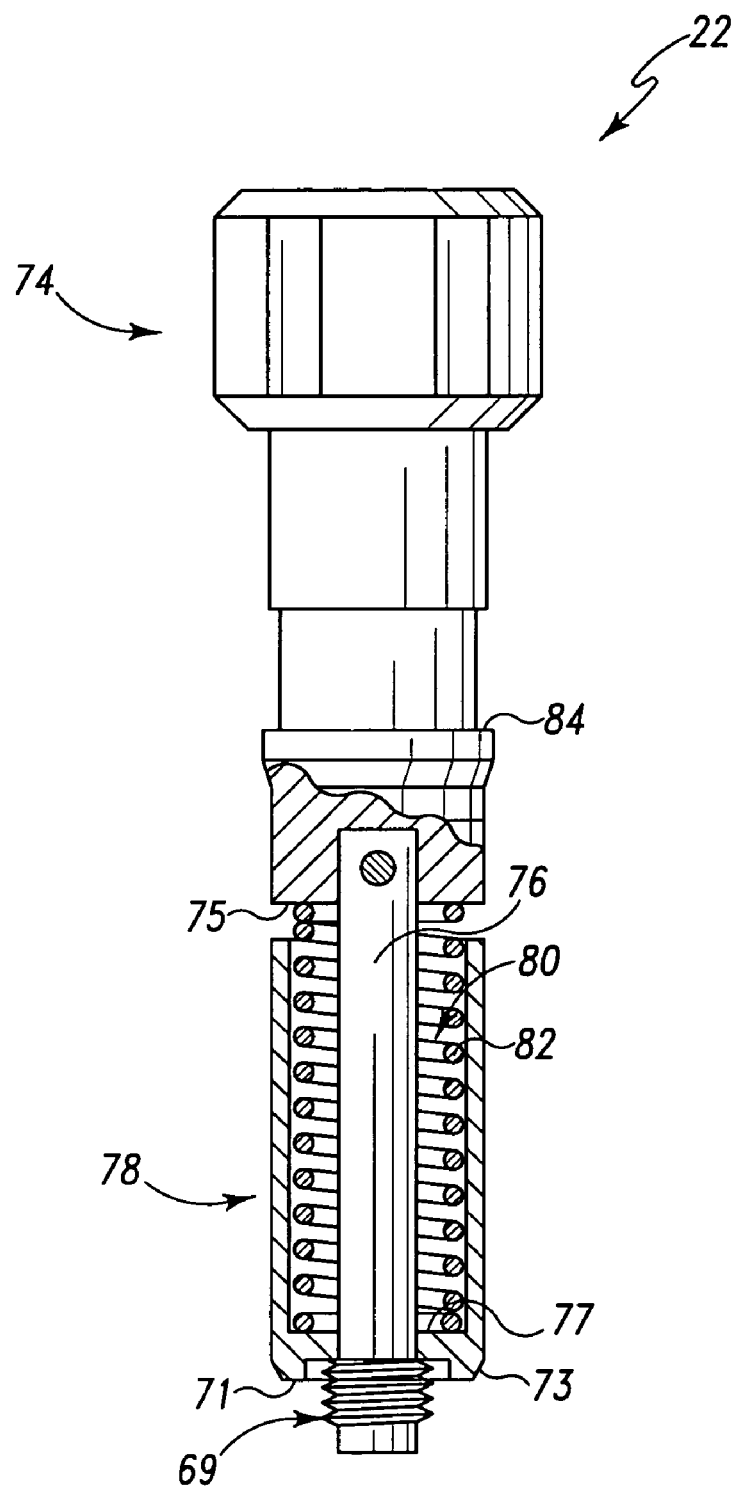
FIG. 5 is a front view, with portions broken away, of a pin of the self-centering coupling device.

As shown in FIG. 5, pin 22 includes a top or head portion 74, a plunger 76 coupled to head portion 74, and a bottom or foot portion 78. Foot portion 78 includes a central cavity 80 formed to receive the plunger 76. A spring 82 is also positioned in the cavity 80 about plunger 76. As shown in FIG. 5, a first end of spring 82 is engaged with a bottom surface 75 of head portion 74 while a second end of spring 82 is engaged with an inner, bottom surface 77 of foot portion 78 to bias the head portion 74 and foot portion 78 in a direction away from one another.

Figure 6:
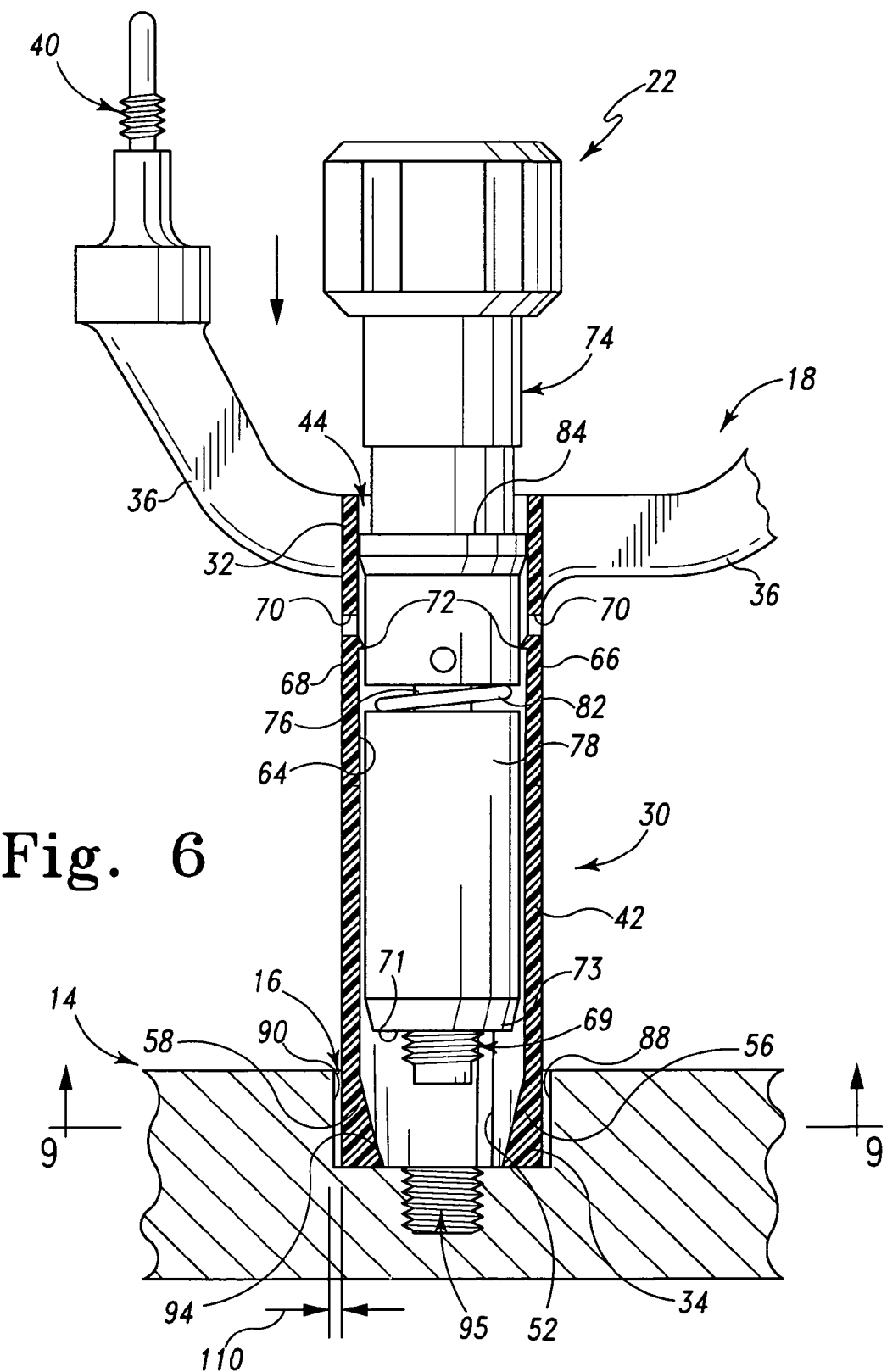
FIG. 6 is a sectional view taken along line 6-6 of FIG. 3 showing the sensor support positioned within a recess of the surgical instrument and showing the pin being inserted into the passageway of the stem of the sensor support.
Figure 7:
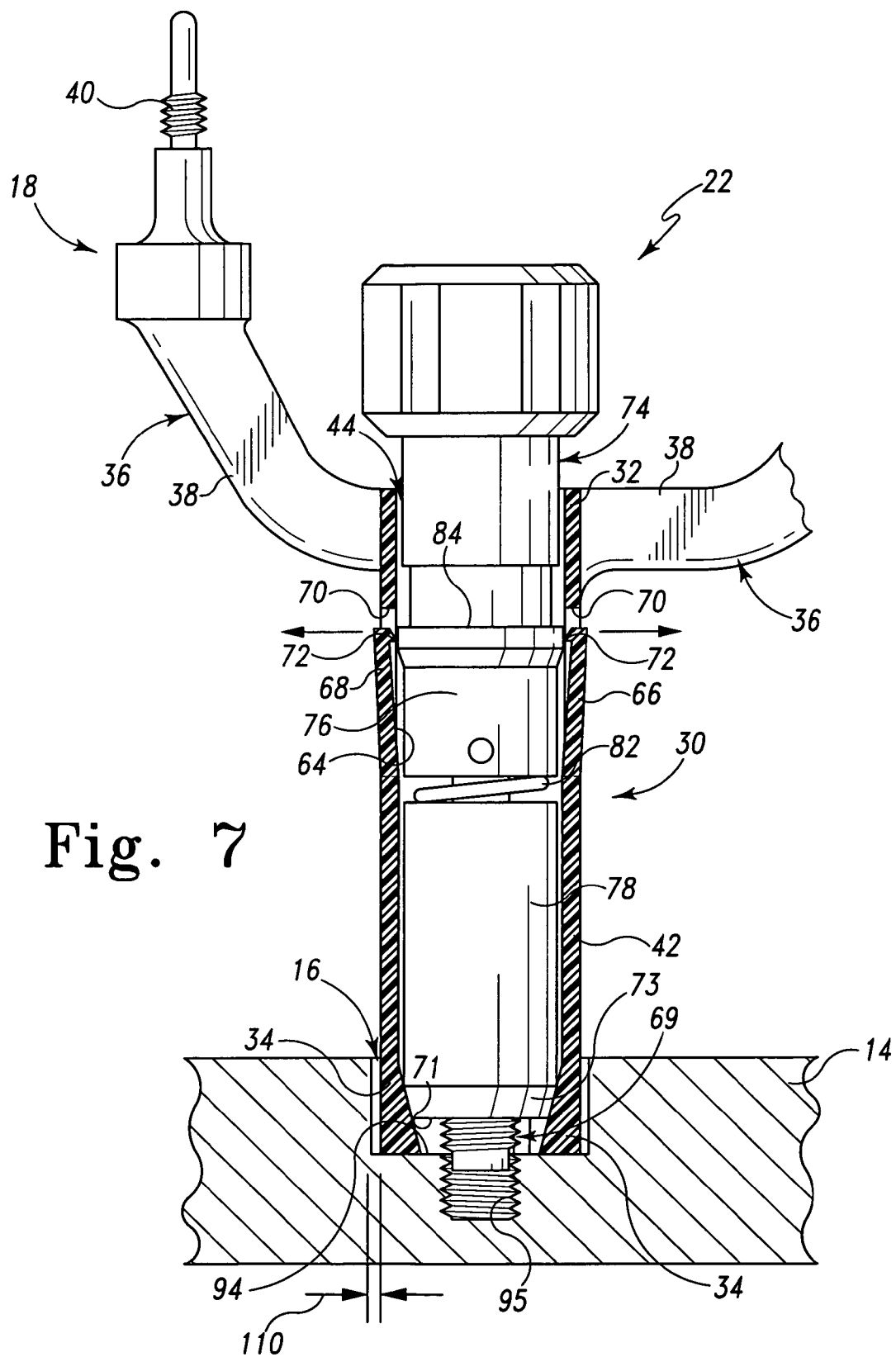
FIG. 7 is a sectional view similar to FIG. 6 showing the fastener inserted farther within the passageway of the sensor support.

Pin 22 further includes an outer rim 84 coupled to head portion 74. As show in FIGS. 6-8, outer rim 84 passes tabs 66, 68 as pin 22 is inserted into passageway 44 of stem 30. As outer rim 84 passes tabs 66, 68, tabs 66, 68 are urged to move outwardly away from each other, as shown in FIG. 7. Once pin 22 is inserted within passageway 44 to a position where the outer rim 84 is positioned below the tabs 66, 68, the lip 72 of each tab 66, 68 helps to maintain the pin 22 within the passageway 44. For example, the outer rim 84 of the pin 22 engages the lip 72 of each tab 66, 68 thereby providing resistance to upward movement of the pin 22 through the passageway 44.

Figure 8:
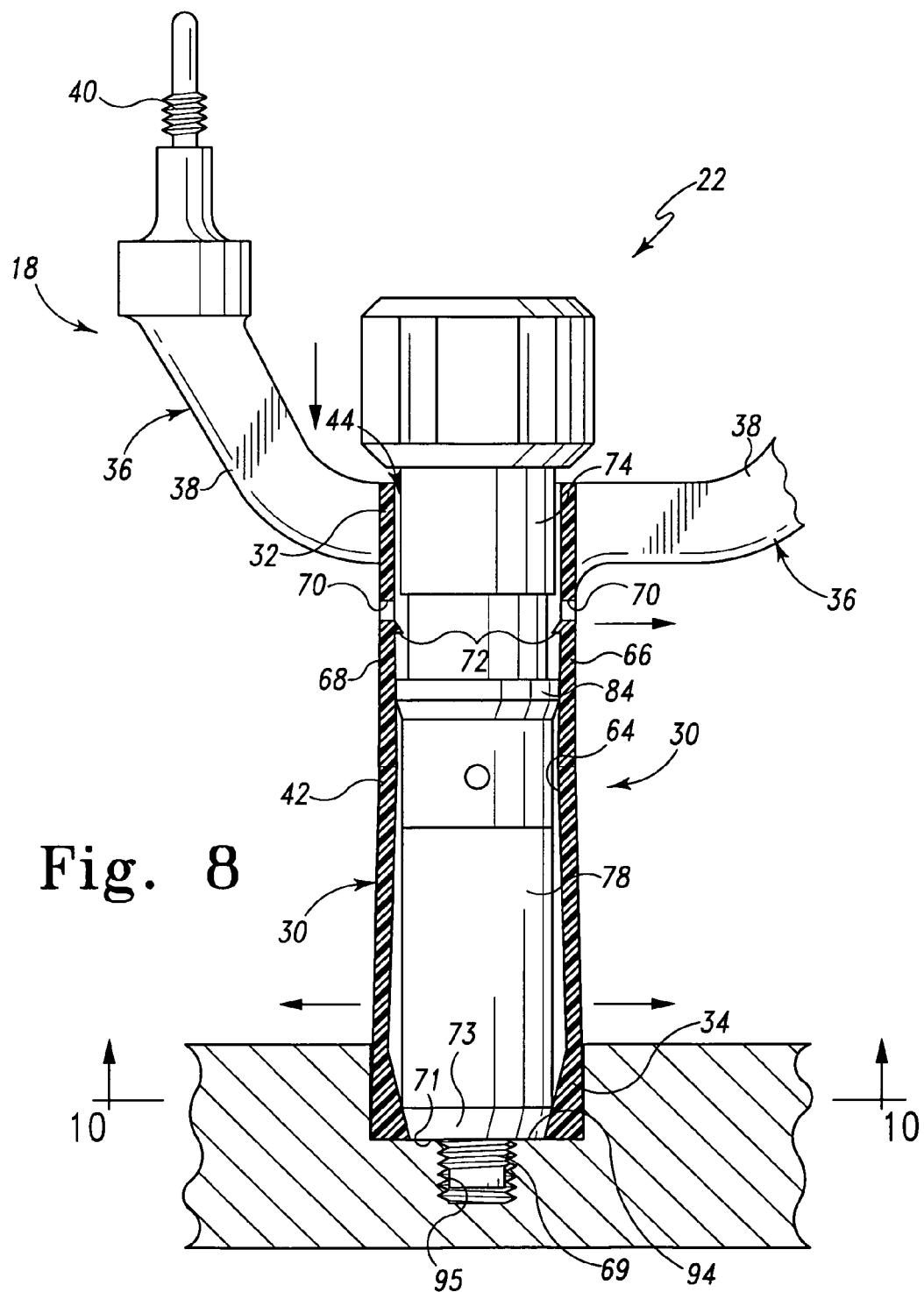
FIG. 8 is sectional view similar to FIGS. 6 and 7 showing the threaded screw of the pin threaded into the threaded bore of the recess formed within the surgical instrument.

A threaded screw 69 of pin 22 is coupled to a proximal end of the plunger 76. Threaded screw 69 extends past a bottom wall 71 of foot portion 78 of pin 22, as shown in FIGS. 6-8. Further, foot portion 78 includes a tapered portion 73 at a proximal end of pin 22. Illustratively, the fastener 22 is made from a metal material such as a cobalt-chrome alloy. However, the pin 22 may be made from other suitable materials such as a plastic, for example.

Looking now to FIGS. 2, 9, and 10, recess or receiver 16 is formed within broach handle 14. Recess 16 may, however, be formed within any surgical instrument intended for use during computer guided orthopaedic surgery. Recess 16 is generally diamond-shaped or tear-drop shaped and is defined by a first pair of opposite, inclined surfaces or side walls 86, 88 which generally form a "V-shape" and a second pair of opposite, inclined surfaces or side walls 90, 92 which also generally form a "V-shape". The first pair of side walls 86, 88 each have a first length and the second pair of side walls 90, 92 each have a second length longer than the first length. Illustratively, as shown in FIGS. 9 and 10, the V-shape of each pair of side walls 86, 88 and 90, 92 is rounded. Recess 16 is further defined by a bottom wall 94 formed in broach handle 14 and coupled to each side wall 86, 88, 90, 92. A threaded bore 95 of recess 16 is formed through bottom wall 94 of recess 16, as shown in FIGS. 6-8. Threaded bore 95 is provided to receive threaded screw 69 of pin 22 therein. Although a threaded bore 95 and corresponding threaded screw 69 are provided, other suitable fasteners or couplers such as a ball-plunger activated quick-connect coupler, for example, may be used as well.

In use, the sensor support 18 may be sterilized and provided in a sterilized package (not shown). In preparation for the computer guided orthopaedic surgery, a surgeon or other member of the surgical team removes the sensor support 18 from the sterile package. The user then secures the sensor support 18 to the surgical instrument to be used during the computer guided orthopaedic surgery, such as the handle 14 of a broach, for example.

To secure the sensor support 18 to the handle 14, the foot portion 100 of the stem 30 is positioned within recess 16. Illustratively, the elongated tear-drop shaped portion of foot portion 100 is positioned between the second pair of longer side walls 90, 92 defining recess 16 such that sensor support 18 is oriented properly with respect to the broach handle 14. As mentioned above, foot portion 100 of stem 30 acts as a key and cooperates with the elongated diamond-shaped recess 16 to provide a single orientation of the sensor support 18 with respect to the broach handle 14.

Once sensor support 18 is properly positioned within recess 16, the pin 22 is inserted within the passageway 44, which is tapered at the proximal end 34 of the stem 30 of the sensor support 18, as shown in FIGS. 6-8, for example. Looking first at FIGS. 6 and 9, prior to pin 22 having been inserted completely into passageway 44, a small space or gap 110 is provided between the proximal end 34 of stem 30 and the respective side walls 86, 88, 90, 92 of recess 16. This excess space, or gap 110 allows stem 30 to be quickly and easily inserted into recess 16. Oftentimes, for example, tight tolerances may hinder a user's ability to quickly and efficiently connect two components together. The additional space or gap 110 provided with the current self-centering coupling device 10 of the present disclosure, therefore, provides a device that is easy to assemble and disassemble.

As pin 22 is inserted further into passageway 44, the tapered end 73 of the pin 22 enters the tapered portion of passageway 44 at the proximal end 34 of the stem 30, as shown in FIG. 7, for example. The diameter of the foot portion 78 of the pin 22 is greater than a diameter of the narrowed, tapered portion of passageway 44. Therefore, as the foot portion 78 enters the tapered portion of the passageway 44, the proximal end 34 of the stem 30 is expanded or otherwise urged outwardly. Specifically, the outer wall portions 56, 58 of the proximal end 34 of the stem 30 are urged away from each other from the position shown in FIG. 9 to the position shown in FIGS. 10 and 8. As the outer wall portions 56, 58 are moved outwardly, the gap 110 between the outer surface of the outer wall portions 56, 58 and the side walls 86, 88, 90, 92 of recess 16 is reduced and eventually closed. As shown in FIG. 10, a portion of first outer wall portion 56 of stem 30 engages side walls 86, 88 of recess 16, and a portion of second outer wall portion 58 of stem 30 engages side walls 90, 92 of recess 16.

This process of expanding the proximal end 34 of stem 30 to the point at which the outer wall 42 of the proximal end 34 of the stem 30 engages the side walls 86, 88, 90, 92 of recess 16 operates to center the stem 30 (and thus the entire sensor support 18) within the recess 16. The self-centering coupling device 10 enables a user to easily and repeatably position the sensors 20 (mounted on the sensor support 18) in substantially the same location on the surgical instrument. Once pin 22 has been fully inserted into passageway 44, the user then rotates the pin 22 to thread the screw tip 69 of pin 22 into the threaded bore 95 of recess 16, as shown in FIG. 8. As pin 22 is rotated in a locking direction and as screw 69 is threaded farther into bore 95, foot portion 78 of fastener 22 engages the bottom wall 94 of recess 16 and acts against the bias of spring 82 to move foot portion 78 and head portion 74 toward each other thereby reducing and/or minimizing the gap between foot portion 78 and head portion 74, as shown in FIG. 8.

Once the sensor stem 30 has been coupled to the broach handle 14 by the fastener 22, the sensor array 12 may be coupled to the sensor stem 30. As discussed above, each spherical sensor 20 is coupled to a corresponding threaded shaft 40 of one of the sensor support arms 36. The sensor array 12 may also be coupled to the sensor stem 30 prior to the sensor stem 30 being inserted into recess 16 formed in broach handle 14. At this point the surgeons and other technicians may perform a computer guided orthopaedic surgical procedure using the broach handle 14, for example, to which the self-centering coupling device 10 has been coupled.

Once the procedure is completed, the pin 22 and the sensor support 18 are removed from the broach handle 14. The sensor support 18 and the sensor array 12 coupled to the first sensor support 18 are disposable and may be discarded after the surgical procedure is completed. As mentioned above in certain embodiments, sensor support 18 is made of a polymeric material, specifically a polycarbonate plastic, and may therefore be used as a one-use, disposable product. However, the sensor support 18 and/or the sensor array 12 may also be re-sterilized and used again for a second computer guided surgical procedure. In an illustrative embodiment, the sensor support 18 is disposed after the procedure, with pin 22 (and perhaps the sensor array 12) being sterilized and reused. As such, prior to a subsequent computer guided orthopaedic surgical procedure, for example, a replacement sensor support 18 may be removed from a sterile package (not shown) and coupled to a surgical instrument using the sterilized pin 22 that was reclaimed and sterilized from the previous procedure.

The invention claimed is:

1. An apparatus for securing a sensor to a surgical instrument for use in computer guided orthopaedic surgery, the apparatus comprising:
    a sensor support having (i) a support arm configured to support the sensor, and (ii) a stem having (a) a first end secured to the support arm, (b) a second end expandable from a first position in which the second end of the stem has a first width and a second position in which the second end of the stem has a second, larger width, and (c) a passageway defined in an inner sidewall of the stem, wherein the inner sidewall of the stem is tapered at the second end of the stem, and
    a pin configured to move the second end of the stem from the first position to the second position, wherein (a) the pin has a tapered end, and (b) insertion of the pin into the passageway causes the tapered end of the pin to engage the tapered inner sidewall of the stem to move the second end of the stem from the first position to the second position.

2. The apparatus of claim 1, wherein:
    the passageway defines a first opening at the second end of the stem when the second end of the stem is positioned in the first position, and
    the passageway defines a second opening at the second end of the stem when the second end of the stem is positioned in the second position, the second opening being larger than the first opening.

3. The apparatus of claim 2, wherein:
    the sensor support arm is a first sensor support arm, and
    the sensor support further comprises a second sensor support arm and a third sensor support arm each coupled to the distal end of the cylindrical stem.

4. The apparatus of claim 3, wherein the first, second, and third support arms each include a threaded shaft configured to receive a sensor for computer guided surgery.

5. The apparatus of claim 1, wherein the second end of the stem has a pair of longitudinal slots defined therein.

6. The apparatus of claim 5, wherein each of the pair of longitudinal slots extends from the second end of the stem toward the first end of the stem a distance less than half a length of the stem.

7. The apparatus of claim 1, wherein the stem is substantially cylindrical in shape and has a lobe extending outwardly from the second end thereof.

8. The apparatus of claim 1, wherein the second end of the stem is tear-drop shaped.

9. The apparatus of claim 1, wherein the stem and the support arm are each constructed with a plastic material selected from the group consisting of: acrylic, epoxy, polyester, polypropylene, polyurethane, polyethylene, polycarbonate, polystyrene, polysulfone, polyetherimide, polyethersulfone, polyphenylsulfone, polyphenylsulfide, acrylonitrile-butadiene-styrene polymer, and polyetheretherketone.

10. The apparatus of claim 1, wherein the stem and the support arm are each constructed with polycarbonate plastic.

11. The apparatus of claim 1, wherein the pin is metallic.

12. The apparatus of claim 1, wherein the stem further includes a lip coupled to an inside surface of the stem and formed to project inwardly into the passageway of the stem, and the pin includes a main body and a rim projecting outwardly from the main body such that the rim of the pin engages the lip of the stem when the pin is positioned within the passageway of the stem.

13. The apparatus of claim 12, wherein the stem further includes a substantially U-shaped cut-out portion formed in an outer wall of the stem and defining a tab of the stem, and wherein the lip is coupled to the tab.

14. The apparatus of claim 1, wherein the pin includes a spring-loaded threaded screw at an end thereof.

15. An apparatus for securing a sensor to a surgical instrument for use in computer guided orthopaedic surgery, the apparatus comprising:
    a support arm configured to support the sensor, and
    a stem having a first end and a second end, wherein (i) the first end of the stem is secured to the support arm, (ii) the second end of the stem is expandable between a first position in which the second end of the stem has a first width and a second position in which the second end of the stem has a second, larger width, and (iii) a passageway is defined in an inner sidewall of the stem, and (iv) the inner sidewall of the stem is tapered at the second end of the stem, and
    a pin configured to move the second end of the stem from the first position to the second position, wherein (i) the pin has a tapered end, and (ii) insertion of the pin into the passageway causes the tapered end of the pin to engage the tapered inner sidewall of the stem to move the second end of the stem from the first position to the second position.

16. The apparatus of claim 15, wherein:
    the passageway defines a first opening at the second end of the stem when the second end of the stem is positioned in the first position, and
    the passageway defines a second opening at the second end of the stem when the second end of the stem is positioned in the second position, the second opening being larger than the first opening.

17. The apparatus of claim 15, wherein the support arm is a first support arm, the apparatus further comprising:
    a second support arm secured to the first end of the stem and a third support arm secured to the first end of the stem.

18. The apparatus of claim 17, wherein the first, second, and third support arms each include a threaded shah configured to receive the sensor for use in computer guided orthopaedic surgery.

19. The apparatus of claim 15, wherein the second end of the stem has a pair of longitudinal slots defined therein.

20. The apparatus of claim 19, wherein each of the pair of longitudinal slots extends from the second end of the stem toward the first end of the stem a distance less than half a length of the stem.

21. The apparatus of claim 15, wherein the stem is substantially cylindrical in shape and has a lobe extending outwardly from the second end thereof.

22. The apparatus of claim 15, wherein the second end of the stem is tear-drop shaped.

23. The apparatus of claim 15, wherein the stem and the support arm are each constructed with a plastic material selected from the group consisting of: acrylic, epoxy, polyester, polypropylene, polyurethane, polyethylene, polycarbonate, polystyrene, polysulfone, polyetherimide, polyethersulfone, polyphenylsulfone, polyphenylsulfide, acrylonitrile-butadiene-styrene polymer, and polyetheretherketone.

24. The apparatus of claim 15, wherein the stem and the support arm are each constructed with polycarbonate plastic.

* * * * *